United States Patent [19]

Meul

[11] Patent Number: 5,166,417
[45] Date of Patent: Nov. 24, 1992

[54] PROCESS FOR RESOLUTION OF RACEMATES OF 2,2-DIMETHYLCYCLOPROPANECARBOXYLIC ACID

[75] Inventor: Thomas Meul, Visp, Switzerland

[73] Assignee: Lonza Ltd., Gampel/Valais, Switzerland

[21] Appl. No.: 750,659

[22] Filed: Aug. 27, 1991

[30] Foreign Application Priority Data

Sep. 4, 1990 [CH] Switzerland ............... 2866/90

[51] Int. Cl.$^5$ ............................... C07B 57/00
[52] U.S. Cl. ........................ 562/401; 562/402; 562/506; 564/359
[58] Field of Search ............... 562/401, 506

[56] References Cited

U.S. PATENT DOCUMENTS

| | | | |
|---|---|---|---|
| 2,388,688 | 11/1945 | Hass | 562/401 |
| 3,666,798 | 5/1972 | Matsui et al. | 562/401 |
| 4,487,956 | 12/1984 | Suzukamo et al. | 560/124 |
| 4,683,089 | 7/1987 | Leigh | 562/401 |
| 4,780,252 | 10/1988 | Leigh | 562/401 |

FOREIGN PATENT DOCUMENTS

| | | |
|---|---|---|
| 0048301 | 3/1982 | European Pat. Off. . |
| 1260847 | 1/1972 | United Kingdom . |
| 1596033 | 8/1981 | United Kingdom . |

OTHER PUBLICATIONS

Chemical Abstract, 99:104949b, (1983).

*Primary Examiner*—Jose G. Dees
*Assistant Examiner*—Vera C. Clarke
*Attorney, Agent, or Firm*—Fisher, Christen & Sabol

[57] ABSTRACT

The enantiomers of 2,2-dimethylcyclopropanecarboxylic acid are separated by salt formation with optically active 1-(3-methoxyphenyl)-ethylamine, fractional crystallization of the diastereomeric salts and subsequent decomposition of the salts with a strong acid.

20 Claims, No Drawings

PROCESS FOR RESOLUTION OF RACEMATES OF 2,2-DIMETHYLCYCLOPROPANECARBOXYLIC ACID

BACKGROUND OF THE INVENTION

1. Field Of The Invention

The invention relates to a process for the production of optically pure 2,2-dimethylcyclopropanecarboxylic acid by resolution of racemates.

2. Background Art

The amide of 2,2-dimethylcyclopropanecarboxylic acid is an important intermediate product for the synthesis of the enzyme inhibitor cilastatin (European Published Patent Application No. 0048301).

Especially for the production of pharmaceutical active ingredients, it is desirable to have 2,2-dimethylcyclopropanecarboxylic acid available in optically pure form, i.e., in the form of the pure (S)-(+) or pure (R)-(−) enantiomer. Since the chemical synthesis of 2,2-dimethylcyclopropanecarboxylic acid yields the compound in the form of its racemate, it is necessary to perform a resolution of this racemate. Such resolutions of racemates are usually performed by first the enantiomer mixture to be separated being converted by an optically active auxiliary substance into a mixture of diastereomeric derivatives which, because of the different physical properties of diastereomers, can be separated by fractional crystallization or chromatography. In the ideal case, a pure enantiomer of the compound to be separated and the optically active auxiliary substance are released from the thus-separated diastereomers.

Actually, with a given auxiliary substance, even if it is optically completely pure, only the incomplete separation of one pure enantiomer is achieved in most cases, so that a mixture remains, which consists predominantly of the other enantiomer. In less favorable cases, neither of the two enantiomers can be isolated in pure form. As derivatives of carboxylic acids for resolution of racemates, their salts with optically active bases, especially amines, are often used. These salts have the advantage that they are formed very easily and quickly and can also again be cleaved by the addition of a strong acid. For resolution of racemates of 2,2-dimethylcyclopropanecarboxylic acid, already (S)-(−)-1-phenylethylamine (British Patent No. 1,260,847), (−)-N-methylephedrine (Japanese Published Patent Application Nos. 60-56936 and 60-56942), quinine (European Published Patent Application No. 0 161 546), and various 1,2-diphenylethylamines (European Published Patent Application No. 0 039 511) have been used.

With 1-phenylethylamine neither a satisfactory yield nor an adequate optical purity could be achieved. Quinine yielded enantiomer in good optical purity but poor yield, no yield was indicated for N-methylephedrine With 1,2-diphenylethylamine the yield is satisfactory and the optical purity very good but the reagent, as is also N-methylephedrine is very expensive. Further, it is known that 2,2-dimethylcyclopropanecarboxylic acid can be separated into the enantiomers by the diastereomeric menthyl esters, which can be obtained from the acid chloride with (+) or (−) menthol (U.S. Pat. No. 4,487,956). This process does provide usable yields and optical purities, but is relatively complicated in working up and requires the relatively expensive menthol.

BRIEF DESCRIPTION OF THE INVENTION

The main object of the invention is to provide a process for resolution of the racemates of 2,2-dimethylcyclopropanecarboxylic acid, which is simple to perform and allows the recovery of both enantiomers in good yield and high optical purity with inexpensive optically active auxiliary substances.

According to the invention, such main object is achieved by the process according to the invention. The process of the invention provides for resolution of the racemates of 2,2-dimethylcyclopropanecarboxylic acid by salt formation with an optically-active amine. 1-(3-Methoxyphenyl)-ethylamine is used as the optically active amine. There is fractional crystallization of the formed diastereomeric salt. Then the diastereomeric salts are reacted with a strong acid, and the released optically-active 2,2-dimethylcyclopropanecarboxylic acid is isolated.

It was found that optically active 1-(3-methoxyphenyl)ethylamine with racemic 2,2-dimethylcyclopropanecarboxylic acid forms diastereomeric salts, which are essentially distinguished by their solubility s that already by single recrystallization the slightly soluble diastereomer can be obtained in largely pure form and in good yield.

Optically-active 1-(3-methoxyphenyl)-ethylamine can be produced by resolution of the racemates of (±)-1-(3-methoxyphenyl)-ethylamine with optically active acids, e.g., malic acid (Japanese Published Patent Application No. 58-041847; Chemical Abstract 99:104949b). (±)-1-(3-methoxyphenyl)-ethylamine can be produced from 3-methoxyacetophenone according to known processes [*Schlittler, E., and Mueller, J.*, Helv. Chim. Acta 31, (1948), pp. 914–924].

The salt formation of the racemic 2,2-dimethylcyclopropanecarboxylic acid with optically active 1-(3-methoxyphenyl)-ethylamine is advantageously performed in a suitable solvent. Suitable solvents are all solvents, in which the two substances are sufficiently soluble and which do not enter into a reaction with one of the two substances, i.e., water and all neutral organic solvents as well as their mixtures. Preferably those solvents are used in which the resulting salts also have a certain solubility so that it is possible to recrystallize the latter from them. Especially preferred is water by itself or in mixture with up to 25 percent by volume of one or more alcohols with 1 to 3 C atoms, i.e., methanol, ethanol, 1-propanol or 2-propanol, especially methanol. As usual in salt formation, the reaction temperature is not critical, preferably the reaction therefore is performed at approximately room temperature.

In using the preferred water/alcohol mixtures as the reaction medium, the amount of solvent is selected preferably so that when the reaction mixture is cooled, for example, to about 0° C., basically only the slightly soluble diastereomer crystallizes out. In this case, it is the diastereomer in which the asymmetric C atoms of acid and amine exhibit opposite configurations, i.e., when using (R)-(+)-1-(3-methoxyphenyl)-ethylamine, the salt with (S)-(+)-2,2-dimethylcyclopropanecarboxylic acid and when using (S)-(−)-amine, the salt with (R)-(−) acid. Then one recrystallization generally is sufficient, and preferably the same solvent is used as was for the salt formation to obtain a product with an optical purity of about 95 percent.

The corresponding enantiomer of 2,2-dimethylcyclopropanecarboxylic acid is released from the resulting diastereomeric salt by the addition of a strong acid. Preferably hydrochloric acid or (aqueous) sulfuric acid is used as the strong acid. This step is preferably performed in water, and the amount of water is suitably selected so that the resultant salt of the strong acid with the amine is completely dissolved.

The main amount of optically active 2,2-dimethylcyclopropanecarboxylic acid precipitates as oil and the part dissolved in the aqueous phase can be recovered by extraction with a nonpolar solvent. As the nonpolar solvent preferably an alkane with 5 to 8 C atoms, i.e., for example, pentane, hexane, heptane, octane, isooctane, cyclohexane or methylcyclohexane, is used which can easily be separated from the 2,2-dimethylcyclopropanecarboxylic acid by distillation. Especially preferred is (n)-hexane. The optically-active 2,2-dimethylcyclopropanecarboxylic acid thus obtained can optionally be converted into the corresponding amide by methods known in the art, for example, by reaction of the acid chloride obtainable from the acid with thionyl chloride with ammonia.

The diastereomeric mixture obtained in the mother liquors of the crystallization steps is advantageously subjected to the same treatment so that from it a mixture of the two enantiomers of 2,2-dimethylcyclopropanecarboxylic acid is obtained, in which the enantiomer, separated with the crystalline salt, is greatly depleted. This enantiomer mixture can now either be reacted with the other enantiomer of 1-(3-methoxyphenyl)-ethylamine to recover the pure other enantiomer and thus be subjected to the process according to the invention or converted into a mixture of the enantiomeric acid chlorides in a way known in the art and be completely racemized by heating to 100° to 200° C.

In the latter case, by hydrolysis of the racemic acid chloride, the racemic 2,2-dimethylcyclopropanecarboxylic acid can again be obtained and fed to the process according to the invention, so that finally, except for unavoidable losses, the entire amount of the racemate can be converted into one pure enantiomer.

The optically active auxiliary substance 1-(3-methoxyphenyl)-ethylene finally can be recovered according to known methods by the addition of a strong base to the salt solution remaining after separation of the 2,2-dimethylcyclopropanecarboxylic acid and extraction.

DETAILED DESCRIPTION OF THE INVENTION

The following examples illustrate the performance of the process according to the invention:

EXAMPLE 1

(R)-1-(3-methoxyphenyl)-ethylammonium-(S)-2,2-dimethylcyclopropane carboxylate 75.9 g of (R)-(+)-1-(3-methoxyphenyl)-ethylamine [[$\alpha$]$_D^{20}$= +22.0 (c=10, MeOH), opt. purity (ee): 98.3 percent] and 57.3 g of ($\pm$)-2,2-dimethylcyclopropanecarboxylic acid were dissolved in a mixture of 750 ml of water and 7.5 ml of methanol at 55° C. and cooled to 0° C. The precipitated crystals were filtered off, dried [dry weight: 45.3 g, [$\alpha$]$_{365}^{20}$: +101.6° (c=3, methanol)], dissolved at 65° C. in a mixture of 314 ml of water and 3.1 ml of methanol, again crystallized out by cooling to 0° C., filtered off and dried. The mother liquor of the recrystallization was again used in the next batch as solvent for the salt formation. Further data concerning the product is:

Yield: 28.4 g
Melting point: 148° to 150° C.
[$\alpha$]$_{365}^{20}$: +130.6° (c=3, methanol)

EXAMPLE 2

(S)-(+)-2,2-dimethylcyclopropanecarboxylic acid 28.4 g of (R)-1-(3-methoxyphenyl)-ethylammonium-(S)-2,2-dimethylcyclopropane carboxylate (from Example 1) was suspended in 60 ml of water and mixed with 11.5 g of 32 percent hydrochloric acid. The (S)-(+)-2,2-dimethylcyclopropanecarboxylic acid precipitated as oil and was extracted twice with 50 ml each of hexane. The hexane phase was concentrated by evaporation in a vacuum and the residue was distilled at 95° C./20 torrs. Further data concerning the product is:

Yield: 12.0 g (20.9 percent, relative to the racemate used)
[$\alpha$]$_D^{20}$: +140.4° (c=1, CHCl$_3$)
Opt. purity (GC): 93 percent

EXAMPLE 3

Working up of the mother liquor and racemizing

The mother liquor resultant in Example 1 of the first crystallization (844.8 g) was mixed with 45.1 32 percent hydrochloric acid and extracted three times with 50 ml each of hexane. 39.4 g of crude (R)-(-)-2,2-dimethylcyclopropanecarboxylic acid [content (GC): 90 percent, [$\alpha$]$_D^{20}$= −51.8° (c=1, CHCl$_3$) corresponding to 39 percent opt. purity] was obtained as a colorless liquid from the hexane phase after distilling off of the solvent. It was diluted with 33.4 g of hexane, heated to 75° C. and within 30 minutes was mixed by instillation with 55.5 g of thionyl chloride in 15.6 g of hexane. After 2.5 hours of stirring at 75° C., the hexane was distilled off at standard pressure and the residue was heated for 2 hours to 135° C. Then, the racemic acid chloride thus obtained was cooled to room temperature, mixed with 140 g of 20 percent sodium hydroxide solution for hydrolysis and heated for one hour to 80° C. The salt solution thus obtained was cooled to room temperature, mixed with 41.1 g of 32 percent of hydrochloric acid and extracted three times with 50 ml each of hexane.

After distilling off the solvent and vacuum distillation of the residue, 29.6 g (83.5 percent, relative to the enantiomer mixture used) of racemic 2,2-dimethylcyclopropanecarboxylic acid was obtained as a colorless liquid.

EXAMPLE 4

Recovery of (R)-(+)-1-(3-methoxyphenyl)-ethylamine

The aqueous phases from Example 2 (87.4 g) and Example 3 (854.4 g), after decomposition of the 1-(3-methoxyphenyl)ethylammonium salts with hydrochloric acid and extraction with hexane, were combined and mixed with 94 g of 25 percent sodium hydroxide solution. The pure amine was extracted three times with 100 ml each of dichloromethane. After distilling off the solvent and vacuum distillation of the residue, 62.1 g of (R)-(+)-1-(3-methoxyphenyl)-ethylamine [content (GC) : 100%, [$\alpha$]$_D^{20}$: 22.0° (c=10, methanol)] was obtained as a colorless liquid.

What is claimed is:
1. (R)-1-(3-methoxyphenyl)-ethylammonium-(S)-2,2-dimethylcyclopropane carboxylate.
2. (S)-1-(3-methoxyphenyl)-ethylammonium-(R)-2,2-dimethylcyclopropane carboxylate.

3. A process for resolution of racemates of 2,2-dimethylcyclopropanecarboxylic acid, comprising forming the diastereomeric salts of the racemates with an optically active amine, the optically active amine being 1-(3-methoxyphenyl)ethylamine, separating the formed diastereomeric salts by fractional crystallization, reacting at least one of the thus-separated diastereomeric salts with a strong acid, and isolating the released optically active 2,2-dimethylcyclopropanecarboxylic acid.

4. The process according to claim 3, wherein the salt formation is performed in water with an addition of 0 to 25 percent by volume of at least on e alkanol with 1 to 3 C atoms as the solvent.

5. The process according to claim 4 wherein the fractional crystallization is performed with water with an addition of 0 to 25 percent by volume of at least one alkanol with 1 to 3 C atoms as the solvent.

6. The process according to claim 5 wherein the salt formation and the fractional crystallization are performed with the same solvent.

7. The process according to claim 6 wherein methanol is used as the alkanol.

8. The process according to claim 7 wherein hydrochloric acid or sulfuric acid is used as the strong acid.

9. The process according to claim 8 wherein the isolation of the optically active 2,2-dimethylcyclopropanecarboxylic acid is performed by extraction with a nonpolar solvent and subsequent distillation.

10. The process according to claim 9 wherein an alkane with 5 to 8 C atoms is used as the nonpolar solvent.

11. The process according to claim 10 wherein hexane is used as the alkane.

12. The process according to claim 10 wherein the process further comprises racemizing the other enantiomer of the 2,2-dimethylcyclopropanecarboxylic acid by (i) converting it into the corresponding acid chloride, (ii) heating the acid chloride to 100° to 200° C. and (iii) hydrolyzing the said acid chloride, and recycling the hydrolyzed acid chloride into the process before the salt formation step.

13. The process according to claim 3 wherein the salt formation is performed in water with an addition of 1 to 25 percent by volume of at least one alkanol with 1 to 3 C atoms as a solvent.

14. The process according to claim 13 wherein methanol is used as the alkanol.

15. The process according to claim 3 wherein the salt formation and the fractional crystallization are both performed with a solvent, which is the same in each step.

16. The process according to claim 3 wherein hydrochloric acid or sulfuric acid is used as the strong acid.

17. The process according to claim 3 wherein the isolation of the optically active 2,2-dimethylcyclopropanecarboxylic acid is performed by extraction with a nonpolar solvent and subsequent distillation.

18. The process according to claim 17 wherein an alkane with 5 to 8 C atoms is used as the nonpolar solvent.

19. The process according to claim 18 wherein hexane is used as the alkane.

20. The process according to claim 3 wherein the process further comprises racemizing the other enantiomer of the 2,2-dimethylcyclopropanecarboxylic acid by (i) converting it into the corresponding acid chloride, (ii) heating the acid chloride to 100° to 200° C. and (iii) hydrolyzing the said acid chloride, and recycling the hydrolyzed acid chloride into the process before the salt formation step.

* * * * *